US005744062A

United States Patent [19]

Dahms et al.

[11] Patent Number: 5,744,062
[45] Date of Patent: Apr. 28, 1998

[54] BALANCED EMULSIFIER BLENDS FOR OIL-IN-WATER EMULSIONS

[75] Inventors: Gerd H. Dahms, Velbert, Germany; James W. Cook, Crystal Lake, Ill.

[73] Assignee: R.I.T.A. Corporation, Woodstock, Ill.

[21] Appl. No.: 705,122

[22] Filed: Aug. 29, 1996

[51] Int. Cl.$^6$ .............................. B01F 17/34; B01J 13/00
[52] U.S. Cl. .................. 252/312; 252/314; 252/315.4; 252/356; 514/873; 514/943; 514/944; 514/975
[58] Field of Search ........................ 252/312, 314, 252/315.4, 356; 514/943, 944, 873, 975

[56] References Cited

U.S. PATENT DOCUMENTS

| | | | |
|---|---|---|---|
| 2,583,576 | 1/1952 | Kern et al. | 252/312 X |
| 2,733,252 | 1/1956 | Thompson et al. | 554/165 |
| 2,789,992 | 4/1957 | Thompson et al. | 554/227 |
| 3,033,686 | 5/1962 | Landfried et al. | 426/573 |
| 3,141,030 | 7/1964 | Buddemeyer et al. | 252/356 X |
| 3,244,534 | 4/1966 | Buddemeyer et al. | 252/356 X |
| 3,472,940 | 10/1969 | Osipow et al. | 424/365 |
| 3,623,887 | 11/1971 | Buddemeyer et al. | 252/356 X |
| 3,728,447 | 4/1973 | Osipow et al. | 424/70 |
| 4,184,978 | 1/1980 | France et al. | 252/309 |
| 4,198,311 | 4/1980 | France et al. | 510/152 |
| 4,804,531 | 2/1989 | Grollier | 514/944 X |
| 4,946,832 | 8/1990 | Goode et al. | 514/943 X |
| 4,992,476 | 2/1991 | Geria | 514/943 X |
| 5,002,680 | 3/1991 | Schmidt et al. | 510/140 |
| 5,011,681 | 4/1991 | Ciotti et al. | 424/81 |
| 5,143,934 | 9/1992 | Lading et al. | 514/943 X |
| 5,221,286 | 6/1993 | Singleton et al. | 514/943 X |
| 5,429,815 | 7/1995 | Faryniarz et al. | 424/47 |
| 5,490,955 | 2/1996 | Hagan et al. | 510/127 |
| 5,496,538 | 3/1996 | Zimmerman et al. | 424/45 |
| 5,575,948 | 11/1996 | Petchul et al. | 252/312 X |
| 5,674,475 | 10/1997 | Dahms et al. | 252/312 X |

Primary Examiner—Richard D. Lovering
Attorney, Agent, or Firm—Marshall, O'Toole, Gerstein, Murray & Borun

[57] ABSTRACT

Balanced emulsifier blends that provide a stable oil-in-water emulsion of preselected viscosity are disclosed. The emulsifier blend contains an acyl lactylate as the primary emulsifier and a nonionic surfactant as the coemulsifier. A method of preparing an oil-in-water emulsion having a preselected viscosity also is disclosed.

19 Claims, 5 Drawing Sheets

| STEP | |
|---|---|
| 1 | USE CORRELATION OF LI WITH VISCOSITY TO SELECT A LACTYLATE FOR THE DESIRED FINAL VISCOSITY |
| 2 | SELECT CO-EMULSIFIERS (FORMULATOR'S CHOICE) |
| 3 | IF > 1 CO-EMULSIFIER, CHOOSE RATIO OF CO-EMULSIFIERS (FORMULATOR'S CHOICE) |
| 4 | CALCULATE HLB OF CO-EMULSIFER BLEND |
| 5 | CHOOSE CO-EMULSIFIER CONCENTRATION (APPROX. 5% FOR CREAMS, APPROX. 2.5% FOR LOTIONS) |
| 6 | CALCULATE REQUIRED USE LEVEL OF SELECTED LACTYLATE USING:<br><br>C=123−30.5HLB−1.35LI+(0.34×HLB×LI) WHERE<br><br>C=WT% LACTYLATE IN TOTAL MIXED EMULSIFIER COMPOSITION<br>HLB=HLB OF CO-EMULSIFIER BLEND<br>LI=LACTYLATE INDEX VALUE OF SELECTED LACTYLATE |
| 7 | COMPOSE DESIRED OIL PHASE AND PICK TOTAL OIL PHASE CONCENTRATION (FORMULATOR'S CHOICE) |

BALANCED EMULSIFIER BLENDS FOR OIL-IN-WATER EMULSIONS

FIELD OF THE INVENTION

The present invention relates to emulsifier blends for oil-in-water (o/w) emulsions. More particularly, the present invention relates to emulsifier blends containing: (a) an acyl lactylate as a primary emulsifier and (b) a nonionic compound capable of forming a gel network in an aqueous phase as a coemulsifier, which provide a stable o/w emulsion of preselected viscosity. The present invention also relates to a method of determining the identity and amount of acyl lactylate to use in conjunction with a particular coemulsifier, and thereby achieve a stable o/w emulsion of desired and predetermined viscosity. More particularly, the method utilizes a lactylate index that predicts the performance of an acyl lactylate in an o/w emulsion.

BACKGROUND OF THE INVENTION

Oil-in-water emulsions traditionally are considered in terms of a two-phase composition having droplets of an oil phase dispersed throughout a continuous aqueous phase, wherein surfactants stabilize the interface between the dispersed oil phase and the continuous aqueous phase, and thickeners impart viscosity to the continuous phase. Recent analyses of o/w emulsions, however, depict an o/w emulsion as a three phase composition containing an oil phase, water, and liquid crystalline (LC) gel network structures. For the majority of relatively dilute o/w emulsions, the emulsifier concentration is considerably in excess of the level required for monolayer coverage at the interface between the oil phase and aqueous phase. The excess emulsifier then aligns in the continuous aqueous phase as lamellar liquid crystals. These liquid crystals add bulk to the continuous phase, and are primarily responsible for both the rheology and the stability of the o/w emulsion.

Figure 1:
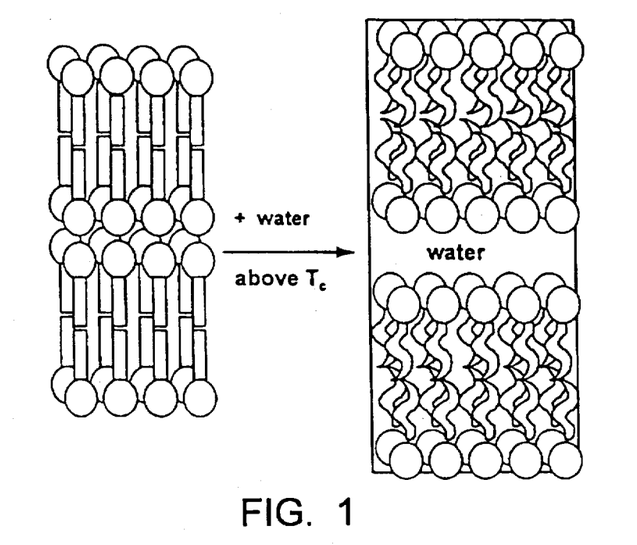
FIG. 1 illustrates the formation of a liquid crystal (LC) lamellar phase in a mixture containing a coemulsifier and water above a critical temperature ($T_c$)
Figure 2:
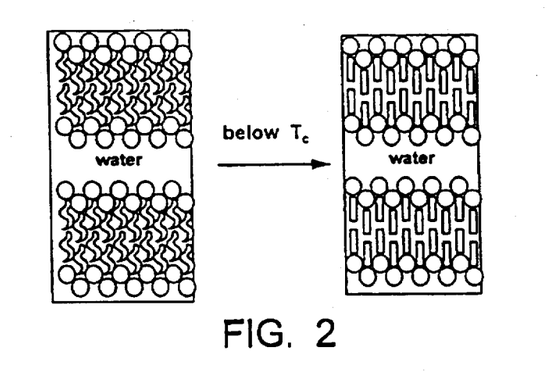
FIG. 2 illustrates the formation of a gel network structure after cooling the LC lamellar phase below the $T_c$.

The primary component of an LC gel network system is traditionally termed "a coemulsifier," e.g., a low HLB (hydrophilic-lipophilic balance) nonionic surfactant having a linear long hydrocarbon chain, and that preferably is solid at room temperature. When mixed with water and heated above its melting points, such coemulsifiers form a lamellar phase. After cooling, gel networks form when the melting point of the hydrocarbon chain of the coemulsifier (i.e., the critical temperature) is approached. Other examples of gel network formers (i.e., coemulsifiers) include: solid fatty acids, solid fatty alcohols, glyceryl monostearate and similar glyceryl esters, solid sorbitan esters, solid polyglycerin esters, and solid methyl glucoside esters. The formation of an LC phase is illustrated in FIGS. 1 and 2, wherein FIG. 1 illustrates the addition of a coemulsifier to water, and heating the resulting mixture above the critical temperature ($T_c$). Above the $T_c$, water becomes inserted between the hydrophilic heads of the coemulsifier and separates the hydrophilic heads. FIG. 2 illustrates cooling of the LC lamellar phase below the $T_c$, which results in formation of a gel network structure.

A gel network formed solely from a coemulsifier, e.g., a low HLB nonionic surfactant, does not effectively emulsify an oil phase in a continuous aqueous phase. The gel network must be "swollen" in order to add body and stability to the o/w emulsion. This traditionally has been accomplished by using a high HLB surfactant, i.e., a primary emulsifier, in conjunction with the coemulsifier. The primary emulsifier can be an anionic, cationic, or nonionic surfactant. When a gel network former (i.e., coemulsifiers) is properly blended with a relatively low amount of a high HLB surfactant (i.e., primary emulsifiers), for example, in a weight ratio of about 4:1 to about 90:1, the gel network "swells," i.e., the size of the trapped water layer between hydrophilic heads of the coemulsifier expands significantly.

Figure 3:
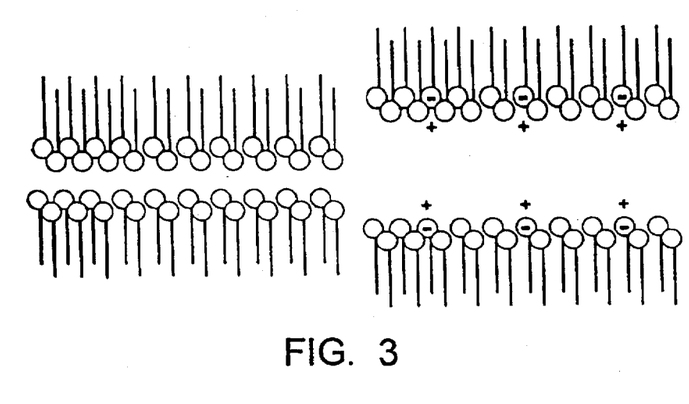
FIG. 3 illustrates the effect of an anionic primary emulsifier on the swelling capacity of a nonionic coemulsifier.

As illustrated in FIG. 3, when a low HLB coemulsifier, such as stearyl alcohol, is properly blended with a high HLB primary emulsifier, the gel network "swells." The "swelling" phenomenon is attributed to stearic effects and/or to electrostatic effects resulting from the electronic charge of an ionic primary emulsifier. Such swollen gel networks stabilize dispersed droplets of the oil phase and thicken the continuous aqueous phase of oil-in-water emulsions.

For each combination of gel network former (i.e., coemulsifier) and "swelling agent" (i.e., primary emulsifier) in a particular o/w emulsion (i.e., an emulsion having a particular electrolyte concentration, pH, and choice of ingredients, for example), there is an optimum ratio of coemulsifier to primary emulsifier to achieve maximum swelling. When maximum swelling is achieved, the emulsifier blend is considered to be "balanced." Individual coemulsifiers and individual primary emulsifiers each have different efficacies (i.e., amount of swelling achieved at optimum use level), and different efficiencies (i.e., amount of swelling per unit of surfactant used) which vary depending upon the particular o/w emulsion. As a result, emulsifier blends can be designed to provide a stable o/w emulsion of desired physical properties.

However, the number of individual coemulsifiers and the number of primary emulsifiers is extremely large, and the potential combinations of coemulsifiers and primary emulsifiers is astronomical. For example, a primary emulsifier can be essentially any high HLB surfactant showing surface activity, such as sodium lauryl sulfate or cetyl pyridinium bromide, and often is an active ingredient in the o/w emulsion. Similarly, the coemulsifier can be any nonionic surfactant having a low HLB.

Until the present invention, formulators could rely only upon serendipity, trial and error, and prior experience in arriving at an emulsifier blend that would provide an o/w emulsion having the desired viscosity, stability, and feel. The only empirical tool available to formulators was the HLB scale for surfactants, which generally indicates to a formulator surfactants that can be used to generate an o/w emulsion, or a water-in-oil emulsion, and surfactants that can be used as foam generators. However, the HLB scale cannot be used when formulating an o/w emulsion based on a blend of emulsifiers. Consequently, the HLB value is not an available tool with respect to formulating a majority of cosmetic o/w emulsions. Therefore, even when using the HLB scale as a guide and starting point, formulators still had to rely on a trial and error method to arrive at an emulsifier blend that provided desired o/w emulsion properties, such as viscosity and feel.

As previously stated, swollen gel networks are achieved by a blend of emulsifiers dispersed in water at a temperature above the melting point of the hydrophobic hydrocarbon chains. At these temperatures, lamellar liquid crystalline structures, which lower the interfacial tension between water and oil to very low values, are formed. Consequently, very small oil phase droplets are formed with a low energy input in the presence of lamellar liquid crystalline phases. During cooling of the aqueous phase or emulsion containing lamellar liquid crystalline phases, the liquid crystalline structure turns into a viscous gel network below the critical hydrophobic chain melting point of the total mixed emulsifier composition. The small droplet size and the high viscosity of the gel network resist creaming, in accordance with Stoke's Law.

Therefore, swollen gel network structures in the aqueous phase stabilize dispersed oil droplets because interfacial tension between the gel network structures and the oil phase is very low. Simultaneously, the gel network structures thicken the aqueous phase because of their quasi-crystalline structure. Thus, the viscosity of an o/w emulsion can be directly increased or decreased through a proper selection of emulsifiers, or by raising or lowering the concentration of emulsifiers in the o/w emulsion.

It would be desirable, therefore, to provide an emulsifier blend that yields a stable o/w emulsion of preselected viscosity without the need to first individually identify a coemulsifier and a primary emulsifier that effectively emulsify the composition, and then determine the proper ratio of emulsifiers by a trial and error method. It would be time saving and economical if the formulator could choose any coemulsifier, and then quickly determine the identity and amount of primary emulsifier to use in conjunction with the coemulsifier to provide a stable o/w emulsion of preselected viscosity. Such a method would obviate time-consuming experimentation. The present invention is directed to such balanced emulsifier blends, and to a method of determining the identity and amount of a primary emulsifier to use with a coemulsifier, and thereby provide a stable o/w emulsion of desired and predetermined viscosity.

SUMMARY OF THE INVENTION

The present invention is directed to balanced emulsifier blends that provide o/w emulsions of preselected viscosity. The emulsifier blend contains a coemulsifier, which can be any nonionic, low HLB organic compound, and a primary emulsifier, which is an acyl lactylate. An o/w emulsion of preselected viscosity can be prepared by selecting a coemulsifier, then, based on the desired viscosity of the o/w emulsion, selecting a proper acyl lactylate. The amount of acyl lactylate used in combination with the coemulsifier is determined from the HLB of the coemulsifier and the identity of the acyl lactylate. The identities and amounts of coemulsifier and primary emulsifier required to provide a balanced emulsifier blend is independent of the identity of the oil phase and the concentration of the oil phase in the o/w emulsion.

The identity of the acyl lactylate used in conjunction with a particular coemulsifier is determined from an empirical lactylate index (LI) developed for the anionic acyl lactylates. The amount of acyl lactylate used in conjunction with a particular coemulsifier is determined from a mathematical formula which correlates the weight percent of acyl lactylate in the emulsifier blend to the LI value of the acyl lactylate and to the HLB value of the coemulsifier.

The above and other advantages and novel features of the present invention will become apparent from the following detailed description of the preferred embodiments of the invention.

DETAILED DESCRIPTION OF THE PREFERRED EMBODIMENTS

A. Components of the O/W Emulsion

The present invention is directed to emulsifier blends comprising: (a) a coemulsifier and (b) a primary emulsifier. The coemulsifier comprises a nonionic organic compound, or blend of nonionic organic compounds, having a relatively low HLB value. The primary emulsifier is an anionic acyl lactylate. The emulsifier blend is used to provide a stable o/w emulsion containing a dispersed oil phase and a continuous aqueous phase.

The emulsifier blend provides stable o/w emulsions having a desired, predetermined viscosity, and the method of selecting the identities and amounts of coemulsifier and primary emulsifier obviates the traditional trial and error method associated with using HLB values. In addition, by using the present method, which relies upon an empirical lactylate index described in detail hereafter, a stable o/w emulsion is achieved essentially independent of the identity and concentration of the dispersed oil phase. The preparation of a stable o/w emulsion of desired viscosity also is independent of the identity of the coemulsifier, as long as the proper acyl lactylate, and amount of acyl lactylate, is used in conjunction with the coemulsifier.

The selection of a proper acyl lactylate is dependent on the desired viscosity of the o/w emulsion. The viscosity of the o/w emulsion is related to the hereafter-described lactylate index (LI), which allows a formulator to select the proper acyl lactylate to achieve a desired viscosity. The proper amount of acyl lactylate required to provide a balanced blend of emulsifiers is related to the LI of the acyl lactylate and the HLB of the coemulsifier. Accordingly, as also described in detail hereafter, the proper amount of acyl lactylate used in conjunction with the preselected nonionic coemulsifier to provide an o/w emulsion of desired viscosity, can be determined from a simple mathematical formula. Therefore, the time-consuming and expensive trial and error method of arriving at an effective emulsifier blend for o/w emulsions is avoided.

(i) The Coemulsifier

In particular, the emulsifier blend contains a coemulsifier that is capable of forming an LC lamellar phase when admixed with water and heated above a critical temperature ($T_c$), i.e., is capable of forming a gel network in an aqueous phase. Cooling the heated water/coemulsifier mixture below the $T_c$ results in formation of a gel network. Coemulsifiers capable of forming such a gel network typically are nonionic organic compounds having a low HLB value. In particular, useful coemulsifiers have an HLB value of about 0 to about 6, and preferably about 0.1 to about 5. To achieve the full advantage of the present invention, the coemulsifier has an HLB value of about 0.2 to about 4. The HLB value of a compound is a well-known term to persons skilled in the art. Furthermore, the HLB value of a particular compound either is published or can be estimated from published formulations. For example, the HLB value of a particular surfactant can be estimated by dividing the weight percent of the hydrophilic portion of the surfactant by five, e.g., for nonionic ethoxylates, the weight percent of oxyethylene in the surfactant.

The weight ratio of the coemulsifier to the acyl lactylate, as well as the total amount of the emulsifier blend in the o/w emulsion, is related to the final desired viscosity of the emulsion, i.e., whether the desired o/w emulsion is a lotion or a cream. As discussed hereafter, an o/w emulsion that is a cream has a viscosity of about 10 Pa.s (Pascal seconds) or greater when determined using a cone and plate viscometry method. To achieve such a viscosity, the amount of coemulsifier in the o/w emulsion traditionally is about 3.5% to about 7%, and preferably about 4% to about 6%, by weight of the o/w emulsifier. To achieve the full advantage of the present invention, the amount of coemulsifier to provide a cream-like o/w emulsion is about 4.5% to about 5.5%, by weight.

If the desired o/w emulsion is a lotion, the emulsion has a viscosity of about 2 to about 10 Pa.s, when measured using a cone and plate viscometry method. To achieve a lotion-type viscosity, the amount of coemulsifier in the o/w emulsion traditionally is about 1% to about 3.5%, and preferably about 1.5% to about 3%, by weight of the o/w emulsion. To achieve a lotion-like viscosity, the amount of coemulsifier is about 2% to about 3% by weight of the o/w emulsion.

In accordance with an important feature of the present invention, the amount and identity of the coemulsifier used in the o/w emulsion is completely at the discretion of the formulator. The choice of coemulsifier is determined by formulator preference, formulator experience, cost, or physical properties of the coemulsifier, such as mildness to skin. As discussed hereafter, it is the selection of a proper acyl lactylate, and in a proper amount, that provides a balanced emulsifier blend, which in turn provides a stable o/w emulsion of preselected viscosity.

Therefore, the identity of the nonionic coemulsifier is not particularly limited. Preferably, the coemulsifier is a solid at room temperature (i.e., about 250° C.). Examples of classes of coemulsifiers which are capable of forming gel networks include, but are not limited to, solid fatty acids (e.g., $C_{12}$ to $C_{22}$ fatty acids), solid fatty alcohols (e.g., $C_{14}$ to $C_{22}$ fatty alcohols), solid glyceryl fatty acid esters, like glyceryl monostearate and similar glyceryl esters, solid sorbitan fatty acid esters, like sorbitan palmitate, solid polyglyceryl fatty acid esters, and solid methyl glucoside fatty acid esters. Examples of specific nonionic coemulsifiers include, but are not limited to, abietic acid, arachidic acid, arachidonic acid, beeswax, beheneth-5, behenic acid, C18–36 acid, C9–11 pareth-3, C11–15 pareth-3, C11–15 pareth-3 oleate, C11–21 pareth-3, C12–13 pareth-3, C12–15 pareth-2, C12–15 pareth-3 through C12–15 pareth-20, capric acid, caproic acid, caprylic acid, ceteareth-2 through ceteareth-20, cetearyl alcohol, ceteth-1 through ceteth-20, cetyl alcohol, coconut acid, coconut alcohol, corn acid, cottonseed acid, dodoxynol-5, glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glycol distearate, glycol hydroxystearate, glycol oleate, glycol ricinoleate, glycol stearate, hydrogenated animal glyceride, hydrogenated coconut acid, hydrogenated cottonseed glyceride, hydrogenated lard glyceride, hydrogenated menhaden acid, hydrogenated palm oil glyceride, hydrogenated soy glyceride, hydrogenated tallow acid, hydrogenated tallow glyceride, hydrogenated vegetable glyceride, hydroxystearic acid, isodeceth-5, isolaureth-3, isosteareth-2, isosteareth-3, isostearic acid, laneth-5, lanolin acid, lard glyceride, laureth-1 through laureth-20, lareth-5 carboxylic acid, lauric acid, lecithin, linoleic acid, linolenic acid, linseed acid, methyl glucose sesquioleate, methyl glucose sesquistearate, myreth-3, myreth-4, myristic acid, nonoxynol-1 through nonoxynol-20, nonyl nonoxynol-5, octoxyglyceryl behenate, octoxyglyceryl palmitate, octoxynol-1 through octoxynol-20, oleic acid, oleth-2 through oleth-20, oleyl alcohol, palmitic acid, palm kernel alcohol, palm oil glyceride, PEG-2 oleate through PEG-5 oleate, pelargonic acid, polyglyceryl-2 diisostearate, polyglyceryl-3 oleate, polyglyceryl-4 oleate, propylene glycol isostearate, propylene glycol hydroxystearate, propylene glycol laurate, propylene glycol myristate, propylene glycol oleate, propylene glycol ricinioleate, propylene glycol stearate, ricinoleic acid, sorbitan diisostearate, sorbitan dioleate, sorbitan isostearate, sorbitan laurate, sorbitan oleate, sorbitan palmitate, sorbitan sesquiisostearate, sorbitan sesquioleate, sorbitan sesquistearate, sorbitan stearate, sorbitan trisostearate, sorbitan trioleate, sorbitan tristearate, soy acid, steareth-2 through steareth-21, stearic acid, sucrose cocoate, sucrose laurate, sucrose stearate, tall oil acid, tallow acid, trideceth-3, undecanoic acid, undecylenic acid, and mixtures thereof.

Numerous other fatty alcohols and glyceryl esters are listed in the CTFA Cosmetic Ingredient Handbook, First Ed., The Cosmetic Toiletry and Fragrance Assn., Inc., Washington, D.C. (1988) at pages 28 and 29, incorporated herein by reference.

(ii) The Primary Emulsifier

In addition to the coemulsifier, the emulsifier blend contains an acyl lactylate as a primary emulsifier to provide a balanced emulsifier system. Acyl lactylates have the general structural formula:

wherein RCO radical is a $C_6$ to $C_{22}$ acyl radical; a is a number from 1 to 3, and typically 1 to 2; M is an alkali metal, an alkaline earth metal, ammonium, or a substituted ammonium group having one or more $C_1$ to $C_3$ alkyl or hydroxyalkyl groups. The preferred RCO acyl radicals are $C_{12}$ to $C_{22}$ acyl radicals.

The acyl lactylates and their method of manufacture are described in various patents, for example, U.S. Pat. Nos. 2,733,252; 2,744,825; 2,789,992; 3,033,686; and 3,141,030. Various acyl lactylates also are available commercially. Commercial acyl lactylates typically are a blend of the monolactylate (i.e., a=1) and the dilactylate (i.e., a=2), and contain small amounts of trilactylate (i.e., a=3). As used herein, the term "acyl lactylate" is defined as either a pure monolactylate, a pure dilactylate, a pure trilactylate, or a commercial mixture containing the mono-, di-, and trilactylates.

Examples of acyl lactylates having the above general structure include, but are not limited to, sodium lauroyl monolactylate, sodium myristoyl monolactylate, sodium decanoyl monolactylate, potassium dodecanoyl monolactylate, potassium dodecanoyl dilactylate, sodium myristoyl dilactylate, sodium lauroyl dilactylate, triethanolammonium dodecanoyl monolactylate, ammonium decanoyl monolactylate, triethanolammonium decanoyl monolactylate, sodium caprooyl lactylate, sodium capryloyl lactylate, sodium caproyl lactylate, sodium isostearoyl lactylate, sodium cocoyl lactylate, sodium lauroyl lactylate, potassium lauroyl lactylate, sodium stearoyl lactylate, sodium behenoyl lactylate, sodium hydroxystearoyl lactylate, and calcium stearoyl lactylate.

For illustrative purposes, the following idealized structures depict sodium stearoyl lactylate and sodium lauroyl lactylate, respectively:

The acyl lactylate is used in conjunction with the coemulsifier to provide a balanced emulsifier blend yielding the desired viscosity and particle size of the o/w emulsion. As previously stated, the formulator can choose any coemulsifier based on personal preference or experience. The identity of the acyl lactylate, or blend of acyl lactylates, is, however, dependent upon the desired viscosity of the o/w emulsion. As discussed in detail hereafter, the formulator first selects a coemulsifier and a desired viscosity of the o/w emulsion. The formulator then selects an acyl lactylate that is capable of providing the desired viscosity. The selection of a proper acyl lactylate is based on a lactylate index (LI) which correlates viscosity of the o/w emulsion to the structural features of the acyl lactylates.

As also discussed in detail hereafter, the formulator then can calculate the proper amount of acyl lactylate to use in conjunction with the coemulsifier in order to provide a balanced emulsifier blend capable of yielding an o/w emulsion of preselected viscosity.

(iii) The Oil Phase

In accordance with an important feature of the present invention, the balanced emulsifier blend is capable of dispersing an oil phase in the o/w emulsion. The ability to disperse the oil phase is essentially independent of (a) the identity of the oil phase and (b) the amount of oil phase. Typically, however, the o/w emulsion contains about 0.5% to about 25%, and preferably about 1% to about 20% of an oil phase, by weight of the o/w emulsion. To achieve the full advantage of the present invention, the o/w emulsion contains about 2% to about 20%, by weight, of an oil phase.

The balanced emulsifier blend of the present invention can effectively emulsify any oil phase, even difficult to emulsify oil phases such as silicone oils. Accordingly, the o/w emulsion can be formulated to contain any of a number of oil phases, like silicones, esters, or hydrocarbons, in order to achieve a desired cosmetic or esthetic effect.

Oil phases that can be dispersed by the present balanced emulsifier blend include, but are not limited to, a volatile or nonvolatile silicone compound, a volatile or nonvolatile hydrocarbon compound, or mixtures thereof. The volatile silicone compounds can be a linear or cyclic polydimethylsiloxane, such as hexamethylsiloxane or a cyclomethicone, available commercially under the tradenames DOW CORNING 200 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.

Volatile hydrocarbon compounds include hydrocarbons having about 10 to about 30 carbon atoms, for example, isododecane and isohexadecane, i.e., PERMETHYL 99A, PERMETHYL 101A, and PERMETHYL 102A, available from Presperse, Inc., South Plainfield, N.J., or an aliphatic hydrocarbon having about 12 to about 24 carbon atoms, and having a boiling point of about 100° C. to about 250° C. One such compound is ISOPAR M (a $C_{13}$–$C_4$ isoparaffin available from Exxon Chemical Co., Baytown, TX). Other exemplary volatile hydrocarbon compounds are depicted in general structural formula (I), wherein n ranges from 2 to 5.

Nonvolatile oil phases include mineral oil, a phenyltrimethicone, or a polydimethylsiloxane having a viscosity at 25° C. of about 6 to about 400 Cs, such as DOW CORNING 556 FLUID or DOW CORNING 200 FLUID, respectively, available from Dow Corning Corp., Midland, Mich.

Other exemplary nonvolatile organic compounds that can be incorporated into the oil phase include, but are not limited to, (1) branched 1-decene oligomers, like 1-decene dimer or a polydecene; and (2) water-insoluble emollients, such as an ester having at least about 10 carbon atoms, and preferably about 10 to about 32 carbon atoms. Suitable esters include those comprising an aliphatic alcohol having about eight to about twenty carbon atoms, and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500 and provides emollient properties. Suitable esters, therefore, include, for example, but are not limited to: (a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentonoate, cetyl octanoate, isocetyl stearate; (b) aliphatic diand triesters of polycarboxylic acids, including, but not limited to, diisopropyl adipate, diisostearyl fumarate, dioctyl adipate, and triisostearyl citrate; (c) aliphatic polyhydric alcohol esters, including, but not limited to, propylene glycol dipelargonate; (d) aliphatic esters of aromatic acids, including, but not limited to, $C_{12}$–$C_{15}$ alcohol esters of benzoic acid, octyl salicylate, sucrose benzoate, and dioctyl phthalate. Numerous other esters are listed in the CTFA Cosmetic Ingredient Handbook, First Ed., The Cosmetic Toiletry and Fragrance Assn., Inc., Washington, D.C. (1988) at pages 24 through 26, incorporated herein by reference.

The oil phase also can comprise oils, such as essential oils, for example, anise oil, balm mint oil, bay oil, bitter almond oil, calendula oil, camellia oil, caraway oil, cardamom oil, chamomile oil, cinnamon oil, cloveleaf oil, clove oil, coriander oil, eucalyptus oil, ginger oil, hops oil, lavender oil, lemongrass oil, lemon oil, lovage oil, matricaria oil, nutmeg oil, ocotea cymbarum oil, orange flower oil, orange oil, parsley seed oil, peppermint oil, pine oil, pine tar oil, rosemary oil, rose oil, rue oil, sage oil, sambucus oil, sandalwood oil, sassafras oil, spearmint oil, sweet marjoram oil, tar oil, tea tree oil, and yarrow oil.

Naturally occurring oils also can be used as the oil phase, for example, apricot kernel oil, avocado oil, butter, C30–46 piscine oil, C10–18 triglycerides, caprylic/capric/isostearic/ adipic triglycerides, caprylic/capric/lauric triglyceride, caprylic/capric/linoleic triglyceride, caprylic/capric/stearic triglyceride, caprylic/capric triglyceride, castor oil, chaulmoogra oil, cherry pit oil, cocoa butter, coconut oil, cod liver oil, corn oil, cottonseed oil, egg oil, ethiodized oil, glyceryl triacetyl hydroxystearate, glyceryl triacetyl ricinoleate, glyceryl tribehenate, glyceryl trioctanoate, glyceryl triundecanoate, grape seed oil, hazel nut oil, hybrid safflower oil, hydrogenated castor oil, hydrogenated coconut oil, hydrogenated cottonseed oil, hydrogenated lard, hydrogenated menhaden oil, hydrogenated palm kernel oil, hydrogenated palm oil, hydrogenated peanut oil, hydrogenated shark liver oil, hydrogenated soybean oil, hydrogenated tallow, hydrogenated vegetable oil, lanolin oil, lard, linseed oil, menhaden oil, mink oil, moringa oil, neatsfoot oil, oleostearine, olive husk oil, olive oil, palm kernel oil, palm oil, peach kernel oil, peanut oil, pengawar djambi oil, pentadesma butter, placental lipids, rapeseed oil, rice bran oil, safflower oil, sesame oil, shark liver oil, shea butter, soybean oil, sunflower seed oil, sweet almond oil, tall oil, tallow, tricaprin, trihydroxystearin, trisononanoin, trisostearin, trilaurin, trilinolein, trimyristin, triolein, tripalmitin, tristearin, vegetable oil, walnut oil, wheat bran lipids, and wheat germ oil.

Another component of the oil phase can be an ultraviolet light absorber, such as allantoin PABA, amsonic acid, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, 3-benzylidene camphor, benzyl salicylate, bornelone, bumetrizole, butyl methoxydibenzoylmethane, butyl PABA, cinoxate, DEA-methoxycinnamate, digalloyl trioleate, drometrizole, ethyl dihydroxypropyl PABA, ethyl diisopropylcinnamate, etocrylene, glyceryl PABA, glycol salicylate, homosalate, isoamyl p-methoxycinnamate, isobutyl PABA, isopropylbenzylsalicylate, isopropyl methoxycinnamate, menthyl anthranilate, menthyl salicylate, octocrylene, octrizole, octyl dimethyl PABA, octyl methoxycinnamate, octyl salicylate, PABA, TEA-salicylate, tripaba panthenol, and mixtures thereof. Ultraviolet light absorbers also can be incorporated into the continuous aqueous phase. In addition, micropigments can be incorporated into the oil phase, or into the continuous aqueous phase.

(iv) The Carrier and Optional Ingredients

The carrier of the o/w emulsion, i.e., the continuous phase, comprises water. The continuous phase, and the oil phase, also can contain optional ingredients to improve the efficacy or esthetics of the o/w emulsion. These optional ingredients include, but are not limited to, dyes, fragrances, preservatives, antioxidants, deodorizing agents, water softening agents, topically active compounds (like skin conditions or hair conditioners), acids, alkalis, buffers, and similar types of compounds. The optional ingredients typically each are included in the o/w emulsion in an amount of 0% to about 5% by weight of the emulsion.

B. The Lactylate Index

Acyl lactylates are effective primary emulsifiers when used in conjunction with a nonionic coemulsifier. The acyl lactylates provide a balanced emulsifier blend that yield a stable gel network o/w emulsion.

The acyl lactylates are a homologous series of mild, anionic surfactants that can be used as efficient emulsifiers in o/w systems and as efficient foaming agents. Until the present invention, there has been no satisfactory way of correlating the structure of an acyl lactylate, such lactylate carbon chain length and identity of cation, to lactylate performance. Furthermore, the HLB values for the lactylates either are undefined, or, where defined, do not rationalize the different behavior exhibited between acyl lactylates. Accordingly, a "lactylate index" (LI) that can classify, explain, and predict the performance of acyl lactylates in o/w emulsions has been derived.

The LI value for a particular acyl lactylate is directly related to the structure of the acyl lactylate and the cation associated with the acyl lactylate. The determination of an LI value is based on the structure of the acyl lactylate, which is derived from an amphiphilic fatty acid. In particular, a fatty acid contains: (a) a fatty hydrocarbon chain that is hydrophobic, and (b) a carboxylic acid group that is hydrophilic. The formation of an acyl lactylate by the condensation of a lactic acid molecule and a fatty acid through esterification increases the hydrophilic character of the fatty acid. The LI index, therefore, is based on the general relationship:

LI=hydrophilic moiety contribution-hydrophobic moiety contribution.

To arrive at the LI, tests were performed using sodium dilactylates having the hydrophilic moiety:

This hydrophilic moiety was empirically assigned a value of 100.

The various hydrophobic moieties also were assigned the following empirical carbon group numbers:

In addition, based upon the hydrophilic moiety of a sodium dilactylate being assigned a value of 100, and that each hydrophobic moiety —CH(CH$_3$)— is assigned a carbon number of −10, each carboxyl group, i.e., COO—, therefore, has a carbon group number of 40.

The carbon group number for a particular acyl lactylate is calculated by adding individual carbon group numbers for each moiety of the acyl lactylate. Therefore, the LI can be expressed as:

LI=100-carbon group number.

It also was found that the cation associated with the acyl lactylate affects the LI value. The contribution of the cation is empirically derived from the position of the cation in the periodic chart of elements, with sodium being assigned a cation number of one. The cation number decreases for elements larger than sodium or having a valence greater than one, i.e., potassium has a cation number of about 0.95, and calcium has a cation number of about 0.90. Because the cation number is based primarily on the valence of the cation and the size of the cation, it is envisioned that magnesium has a cation number of about 0.95, and ammonium has a cation number of about 0.90 to about 0.95. Ammonium substituted with alkyl and/or hydroxyalkyl groups have a cation number that is dependent on the size and number of the alkyl and/or hydroxyalkyl groups.

To incorporate the contribution of the cation to the LI value, the LI value is expressed as:

LI=(100×cation number)-carbon group number.

It should be understood that although the LI relationship for acyl lactylates was derived from the structure of an acyl dilactylate, a modification of the hydrophilic moiety of the acyl lactylate does not affect the LI. Therefore, the relationship between LI value and structure of the acyl lactylate is valid for monolactylates, dilactylates, trilactylates, and mixtures thereof, as well as analogs of acyl lactylates, wherein a portion or all of the lactic acid used to esterify the fatty acid is replaced with a different α-hydroxy acid or an amino acid. Examples of α-hydroxy acids include, but are not limited to, glycolic acid, citric acid, tartaric acid, malic acid, ethylglycolic acid, mandelic acid, and leucic acid. Examples of amino acids include, but are not limited to, alanine, glutamic acid, threonine, proline, leucine, glycine, tyrosine, and lysine.

Therefore, a generalized LI relationship, which accounts for lactylates and lactylate analogs is:

$$LI = (HC_n \times \text{cation number}) - LC_n$$

wherein $HC_n$ is the contribution from the hydrophilic portion of the acyl lactylate, or an acyl lactylate analog, and $LC_n$ is the contribution from the lipophilic portion of the compound.

This relationship, using cation numbers and carbon group numbers, permits the calculation of an LI value for each acyl lactylate or acyl lactylate analog. Examples of the LI values for selected acyl lactylates are set forth in Table 1.

TABLE 1

| Acyl Lactylate | LI Value |
| --- | --- |
| Sodium caprooyl lactylate | 88 |
| Sodium capryloyl lactylate | 84 |
| Sodium caproyl lactylate | 80 |
| Sodium isostearoyl lactylate | 79 |
| Sodium cocoyl lactylate | 77 |
| Sodium lauroyl lactylate | 76 |
| Potassium lauroyl lactylate | 71 |
| Sodium stearoyl lactylate | 64 |
| Sodium behenoyl lactylate | 56 |
| Sodium hydroxystearoyl lactylate | 44 |
| Calcium stearoyl lactylate | 28 |

As illustrated in Table 1, the LI value for sodium lauroyl lactylate is 76. The structure for sodium lauroyl lactylate is set forth above. The LI value for sodium lauroyl lactylate, therefore, is calculated as follows:

$HC_n = (3 \times 40) + (2 \times (-10)) = 100$ (i.e., 3 $CO_2^-$ moieties, and 2—$CH(CH_3)$—moieties)

Na=1 (cation number for sodium)

$LC_n = 4 + (2 \times 10) = 24$ (i.e., one $CH_3$ moiety and 10—$CH_2$— moieties)

$LI = 100(1) - 24 = 76$.

The LI value for sodium stearoyl lactylate is calculated as follows:

$HC_n = (3 \times 40) + (2 \times (-10)) = 100$

Na=1

$LC_n = 4 + (2 \times 16) = 36$ $LI = 100(1) - 36 = 64$.

The LI value for any acyl lactylate can be similarly calculated. However, it must be noted that a divalent cation, like calcium, is associated with two acyl lactylate anions. Therefore, both acyl lactylate anions are considered in the calculation of LI value. Accordingly, calcium stearyl lactylate has an LI value of about 28.

In deriving the LI relationship to acyl lactylate structure, the contributions to carbon group number were derived from gel network viscosity values. The viscosity values then were set empirically to provide LI values in the 0 to 100 scale. The cation values were derived by direct comparison of gel network viscosities.

Based on the above LI values, the potential end uses for individual acyl lactylates can be predicted, as set forth in Table 2.

TABLE 2

| LI Value | End Use |
| --- | --- |
| 100–90 | Emollients |
| 90–75 | Foaming agents, foam stabilizers |
| 80–50 | o/w emulsifiers |
| 60–30 | Emulsifiers for multiple emulsions |
| 30–0 | Oil gelling agents |

Table 2 shows that an acyl lactylate having an LI value of about 50 to about 80 can be used in an o/w emulsifier. It should be noted that two or more acyl lactylates can be blended to arrive at a desired LI value. Accordingly, the LI value for a blend of acyl lactylates can be determined by the following formula:

$$LI = (wt\ \%A)(LI_A) + (wt\ \%B)(LI_B),$$

wherein wt %A and wt %B are the weight percents of acyl lactylates A and B in the blend, and $LI_A$ and $LI_B$ are the LI values for acyl lactylates A and B, respectively. Therefore, an acyl lactylate having an LI value greater than about 80, or less than about 50, can be used in an o/w emulsion, as long as the acyl lactylate is blended with a second acyl lactylate, and the LI value of the acyl lactylate blend is about 50 to about 80.

The LI allows acyl lactylates to be categorized for different end uses, but also defines quantitative relationships between LI value viscosity, and n viscosity, and the optimum concentration of an acyl lactylate to use in an emulsifier blend. As previously stated, the acyl lactylates are primary emulsifiers, i.e., they swell the water gap in the lamellar liquid crystals formed by the coemulsifier.

To examine the behavior of acyl lactylates as a class, various acyl lactylates were formulated into a standardized o/w emulsion containing 10 wt % of an oil phase, 7.5 wt % of an emulsifier blend, 0.5 wt % preservative, and the balance (82 wt %) water. The 7.5 wt % emulsifier blend contained stearyl alcohol (i.e., the coemulsifier) and an acyl lactylate. For each acyl lactylate, the ratio of acyl lactylate to stearyl alcohol was balanced to achieve maximum swelling of the water gap. Swelling was monitored by viscosity measurement on a cone and plate rheometer. At maximum swelling, the viscosity of the o/w emulsion as a function of acyl lactylate concentration also was a maximum. This series of experiments was performed using three different oil phases: a polydimethylsiloxane silicone fluid of 350 cps, capric/caprylic triglyceride, and sunflower oil. These three oil phases have different oil polarities, and illustrate the influence of pure natural ester oils.

The acyl lactylates used in these tests were sodium behenoyl lactylate, sodium stearoyl lactylate, sodium cocoyl lactylate, sodium caproyl lactylate, sodium caprooyl lactylate, and sodium capryloyl lactylate. These six acyl lactylates provide a homologous series for the hydrophobic carbon chain of the acyl lactylate. To evaluate the influence of the cation, a comparison was made between sodium lauroyl lactylate and potassium lauroyl lactylate.

The optimum ratio of acyl lactylate to stearyl alcohol was determined by rheologic and microscopic characterization. At the optimum ratio, the viscosity of the o/w emulsion reaches a maximum value, and no unswollen vesicles of stearyl alcohol are observed microscopically. The experiments showed that the optimum ratio of acyl lactylate to stearyl alcohol is related to the hydrocarbon chain length of the acyl lactylate. It also was found that, as the hydrocarbon chain length of the acyl lactylate increases, the acyl lactylate use concentration also increases. However, acyl lactylates having a hydrocarbon chain of less than twelve carbon atoms provided o/w emulsions having a low heat stability. Therefore, to provide a heat stable o/w emulsion, preferred acyl lactylates have a hydrocarbon chain of about twelve carbon atoms or greater, e.g., about $C_{12}$ to about $C_{22}$.

In these tests, the following blends of acyl lactylate and stearyl alcohol provided a maximum viscosity. Each o/w emulsion contained a total of 7.5% by weight emulsifier blend. The basic o/w emulsion formulation further contained 82% demineralized water, 0.5% preservative, and 10% of an oil phase. The tests showed that increasing the hydrocarbon chain length of the acyl lactylate requires more of the acyl lactylate in relation to the coemulsifier to achieve maximum viscosity, i.e., to provide a balanced ratio of acyl lactylate to coemulsifier.

| | |
|---|---|
| Sodium behenoyl ($C_{22}$) lactylate | 3.00 |
| Stearyl alcohol | 4.50 |
| Sodium stearoyl ($C_{18}$) lactylate | 2.50 |
| Stearyl alcohol | 5.00 |
| Sodium Cocoyl ($C_{12}$–$C_{14}$) lactylate | 1.50 |
| Stearyl alcohol | 6.50 |
| Sodium lauroyl ($C_{12}$) lactylate | 1.13 |
| Stearyl alcohol | 6.37 |
| Sodium caproyl ($C_{10}$) lactylate | 1.10 |
| Stearyl alcohol | 6.40 |

Figure 4:
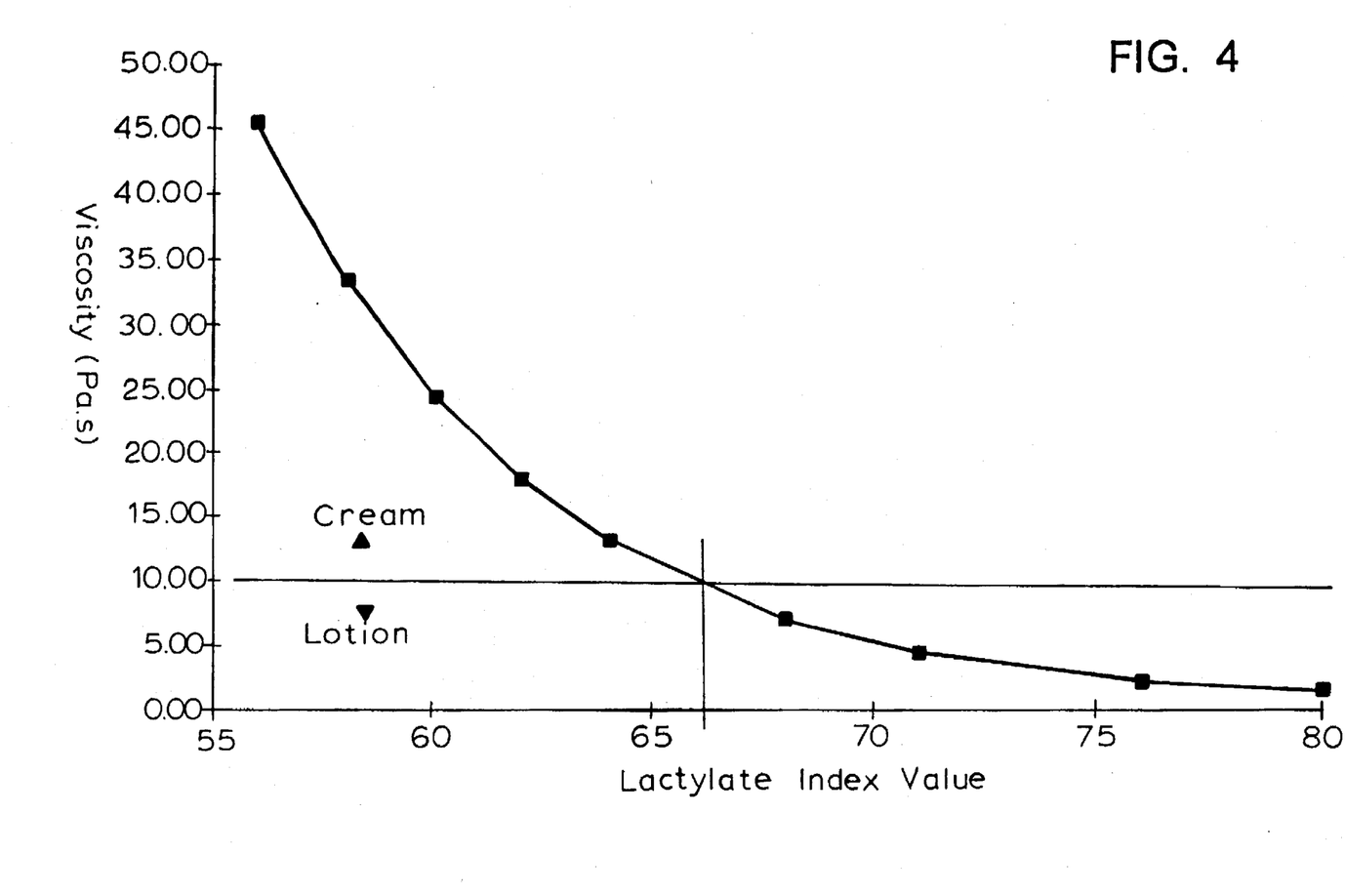
FIG. 4 is a plot of viscosity (in Pa.s) vs. lactylate index (LI) showing that viscosity of an o/w emulsion decreases as LI increases.

Tests on the basic formulation containing 10% oil phase and 7.5% stearyl alcohol/acyl lactylate also revealed that the carbon chain length of the hydrophobic moiety of an acyl lactylate has an impact on the gel network structure formed with stearyl alcohol, and consequently on the viscosity and yield stress of the o/w emulsions. In particular, FIG. 4 is a plot of LI value vs. viscosity of the o/w emulsion in Pa.s using a cone and plate viscometer. The plot in FIG. 4 shows that for increasing LI values, the viscosity of the o/w emulsion decreases. In addition, it is known that an o/w emulsion having a viscosity of greater than about 10 Pa.s is a cream, whereas an emulsion having a viscosity of less than about 10 Pa.s is a lotion. Therefore, if a formulator needs to design a cream-like product, an acyl lactylate having an LI value of about 66 or less is selected as the acyl lactylate. If the desired product is a lotion, the formulator selects an acyl lactylate having an LI value of about 66 or greater.

FIG. 4 further shows that a formulator can preselect a desired viscosity, then choose an acyl lactylate, or a blend of acyl lactylates, having the correct LI value to provide the desired viscosity. Furthermore, although the plot in FIG. 4 was derived from an o/w emulsion containing 7.5 wt % of an emulsifier blend, the mixed emulsifier system containing the acyl lactylate and stearyl alcohol can be reduced to as low as 2 wt %, as long as the optimum ratio between the acyl lactylate and stearyl alcohol is maintained. The viscosity of the o/w emulsions then follows the mathematical formula:

wherein $\eta$ is viscosity in Pa.s, $C_E$ represents concentration of the emulsifier blend containing the acyl lactylate and stearyl alcohol, and K is a specific constant of the formulation.

In addition, the stearyl alcohol used as the coemulsifier can be partly or totally replaced by other coemulsifiers, such as glyceryl monostearate, a polyglycerin ester, or other solid fatty alcohols. As discussed hereafter, in such a case, the use concentration of the acyl lactylate varies with the HLB of the coemulsifier, wherein the higher the HLB value of the coemulsifier, the lower the use concentration of the acyl lactylate. Therefore, a partial replacement of the stearyl alcohol with glyceryl monostearate leads to a reduction of the acyl lactylate concentration.

The relationship illustrated in the plot of FIG. 4 also can be expressed linearly. Tests have shown that a direct mathematical relation exists between the carbon chain length (C) of the acyl lactylate, and the final o/w emulsion viscosity ($\eta$) or the yield stress ($\tau$), i.e., $\eta = kc^n$ or $\log \eta = \log k + n \log c$; and $\tau = kc^n$ or $\log \tau = \log k + n \log c$, wherein k and n vary slightly with the identity of the oil phase.

For the base formulations that were tested, the mathematical formulae were:

$$\eta = 2.85 \times 10^{-5} \, c^{4.57}, \text{ and}$$

$$\tau = 5.49 \times 10^{-2} \, c^{1.91},$$

wherein $\eta$ is in Pa.s units and $\tau$ is in Pa units. The logarithm of the carbon chain length can be expressed as the LI value by using the definition of LI. Then, the optimum viscosity of the swollen basic formulations in these experiments can be expressed as:

$$\log \eta = 12.6 - (0.16 \times LI) \text{ for ester oils}$$

$$\log \eta = 12.5 - (0.16 \times LI) \text{ for silicone oils,}$$

wherein $\eta$ (viscosity) is expressed in Pa.s.

The above two equations show that the viscosity of the o/w emulsion is essentially independent of the identity of the oil phase. Accordingly, regardless of the oil phase present in the o/w emulsion, the viscosity of the emulsion can be expressed as:

$$\log \eta = 12.6 - (0.16 \times LI).$$

Conversely, if a preselected viscosity ($\eta$) is desired, this viscosity can be attained by substantially satisfying the above formula, i.e, by selecting an acyl lactylate having an LI to provide about 0.9 log $\eta$ to about 1.1 log $\eta$, and preferably about 0.95 log $\eta$ to about 1.05 log $\eta$.

This equation shows that the carbon chain length of the hydrophobic moiety of an acyl lactylate exerts a major influence on the gel network structure of an o/w emulsion formed from stearyl alcohol, and, consequently, on the viscosity and yield stress of the o/w emulsions. The tests also showed that acyl lactylates having a hydrocarbon chain length below about $C_{10}$ are inferior as primary emulsifiers, and are not preferred in o/w emulsions.

Figure 5:
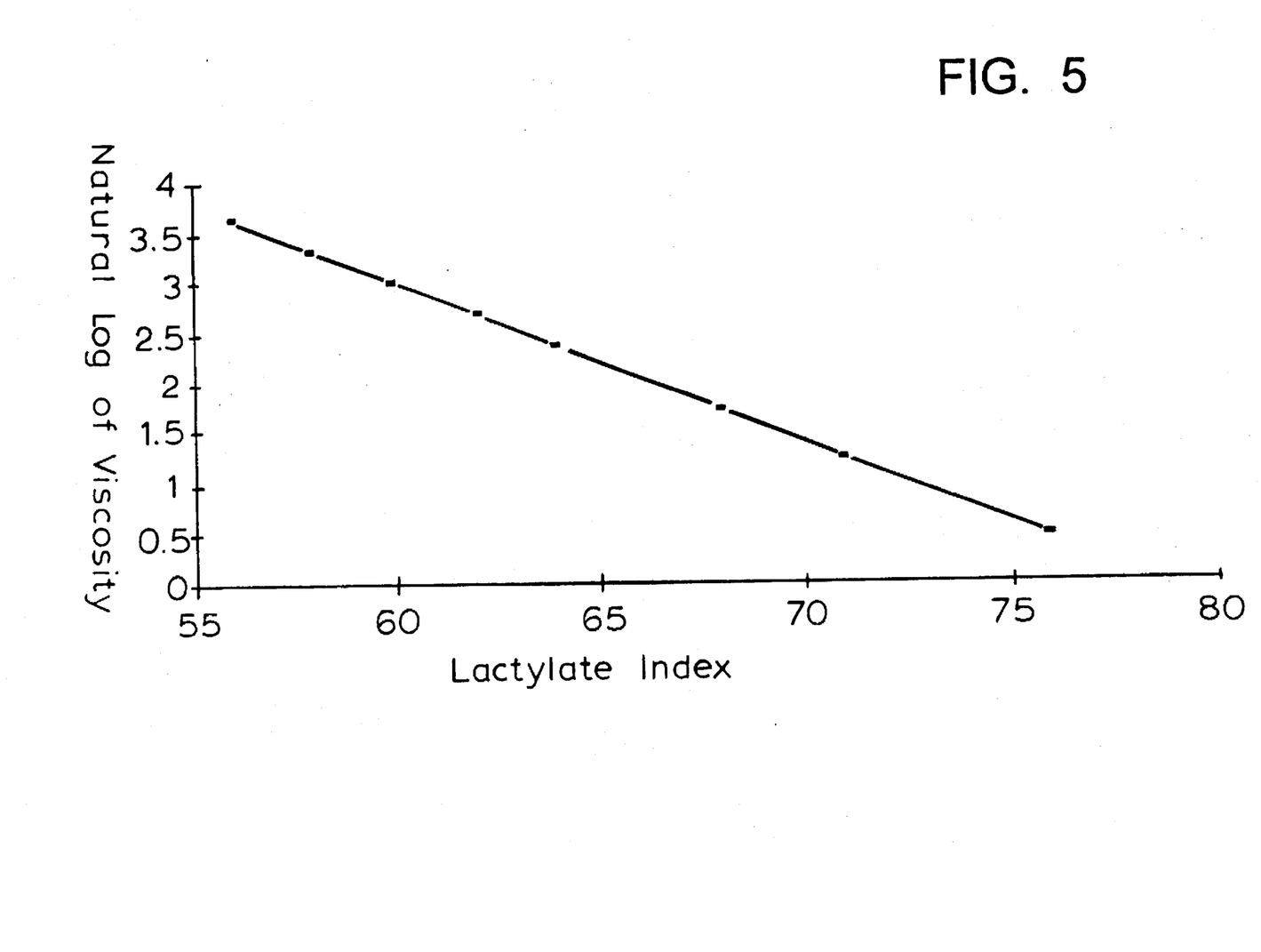
FIG. 5 is a plot of natural log of viscosity of an o/w emulsion vs. LI showing the linear decrease in viscosity with an increase in LI.

The linear relationship between lactylate index and the viscosity of the o/w emulsion is illustrated in the plot of FIG. 5. FIG. 5 contains a plot of LI values vs. natural log of o/w emulsion viscosity. Tables 3–6 show that the plot in FIG. 5 correlates the predicted viscosity for an acyl lactylate of particular LI value to experimental viscosity measurements.

TABLE 3

| Ester Oil Phase LI | Measured Viscosity [Pa.s] | Calculated Viscosity [Pa.s] |
| --- | --- | --- |
| 56 | 37.05 | 38.09 |
| 58 |  | 27.66 |
| 60 |  | 20.09 |
| 62 |  | 14.59 |
| 64 | 17.00 | 10.59 |
| 68 |  | 5.58 |
| 71 | 3.29 | 3.46 |
| 76 | 2.63 | 1.55 |
| 80 | 1.00 | 0.82 |

TABLE 4

| Ester Oil Phase LI | Ln Measured Viscosity | Ln Calculated Viscosity |
| --- | --- | --- |
| 56 | 3.61 | 3.64 |
| 58 |  | 3.32 |
| 60 |  | 3.00 |
| 62 |  | 2.68 |
| 64 | 2.83 | 2.36 |
| 68 |  | 1.72 |
| 71 | 1.19 | 1.24 |
| 76 | 0.97 | 0.44 |
| 80 | 0.00 | −0.20 |

TABLE 5

| Silicone Oil Phase LI | Measured Viscosity [Pa.s] | Calculated Viscosity [Pa.s] |
| --- | --- | --- |
| 56 | 30.81 | 34.47 |
| 58 |  | 25.03 |
| 60 |  | 18.17 |
| 62 |  | 13.20 |
| 64 | 22.70 | 9.58 |
| 68 |  | 5.05 |
| 71 | 2.51 | 3.13 |
| 76 | 2.14 | 1.40 |
| 80 | 1.09 | 0.74 |

TABLE 6

| Silicone Oils LI | Ln Measured Viscosity | Ln Calculated Viscosity |
| --- | --- | --- |
| 56 | 3.43 | 3.54 |
| 58 |  | 3.22 |
| 60 |  | 2.90 |
| 62 |  | 2.58 |
| 64 | 3.12 | 2.26 |
| 68 |  | 1.62 |
| 71 | 0.92 | 1.14 |
| 76 | 0.75 | 0.34 |
| 80 | 0.08 | −0.30 |

The correlation between lactylate index and o/w emulsion viscosity was determined using the above-described basic formulation, but the correlation is universal for all o/w emulsions containing an acyl lactylate as the primary emulsifier. The viscosity of an o/w emulsion is only very weakly related to the chemical composition of the oil phase, the phase volume fraction of the oil phase, and the droplet size of the oil phase. The nature of the LC gel network is primarily responsible for ultimate emulsion rheology. In turn, the choice of acyl lactylate exerts a primary influence on the LC gel network, and, thus, of whether the o/w emulsion is a solid cream, soft cream, thick lotion, or thin lotion.

Furthermore, if viscosity units other than Pa.s are used, the constants in the correlation change. Likewise, for different measurement conditions or different rheometers (i.e., Brookfield vs. cone and plate), the constants in the correlation change. However, the existence of a linear correlation does not change. The formulator, therefore, can construct a correlation for viscosity measurements using any method or rheometer by measuring the viscosity of the following two formulations, and drawing a straight line connecting the plotted points.

| | |
| --- | --- |
| sodium stearoyl lactylate | 2.37 wt % |
| cetearyl alcohol | 5.13 |
| ester oil phase | 10.00 |
| demineralized water | 82.50 |
| sodium lauroyl lactylate | 1.13 wt % |
| cetearyl alcohol | 6.37 |
| ester oil phase | 10.00 |
| demineralized water | 82.50 |

The tests performed on the basic formulation also showed that o/w emulsion stability increases as the carbon chain length of the acyl lactylate increases, that potassium acyl lactylates provide higher viscosities than sodium acyl lactylates, and that hydrocarbon chain length of the acyl lactylate is not related to skin feeling.

The LI also permits the formulator to calculate the amount of acyl lactylate to incorporate into an emulsifier blend to provide a balanced emulsifier blend. The calculation relies primarily on the LI value of the acyl lactylate and secondarily on the HLB value of the coemulsifier.

In designing a balanced emulsifier blend, the formulator first selects a coemulsifier, i.e., either a single nonionic surfactant or a nonionic surfactant blend, and calculates the HLB of the coemulsifier. The HLB value of the coemulsifier either is published or can be determined by methods well known in the art. The choice of coemulsifier is arbitrary, i.e., the choice based on formulator familiarity with the coemulsifier, dermatological profiles, company practice, or other considerations. As previously stated, the formulator is not limited in a selection of coemulsifier, except that the coemulsifier is capable of forming a gel network in an aqueous phase.

After choosing a coemulsifier, for example, a blend of glyceryl monostearate and cetostearyl alcohol, in any ratio, the formulator calculates the HLB of the blend, and then selects the acyl lactylate primary emulsifier by using the LI to choose an acyl lactylate that provides a desired, preselected viscosity. The selection of a proper acyl lactylate is facilitated by FIGS. 4 and 5, which correlate LI values to o/w emulsion viscosity. Then, the proper concentration of acyl lactylate is calculated using the LI.

The concentration of acyl lactylate is determined according to the following equation:

$$C_L = 105.34 - (1.15 \times LI)$$

wherein $C_L$ is the concentration of the acyl lactylate in the emulsifier blend, in wt %. This concentration is different from the amount of acyl lactylate in the final o/w emulsion, which is discussed hereafter. The basis for arriving at the acyl lactylate concentration equation is set forth in the data summarized in Table 7.

TABLE 7

| LI | Measured Concentration | Calculated Concentration (wt % lactylate in total mixed emulsifier system) |
|---|---|---|
| 56 | 40 | 40.9 |
| 58 |  | 38.6 |
| 60 |  | 36.3 |
| 62 |  | 34.0 |
| 64 | 33.3 | 31.7 |
| 68 |  | 27.1 |
| 71 |  | 23.7 |
| 76 | 15.1 | 17.9 |
| 80 | 14.7 | 13.3 |

The acyl lactylate concentration equation was derived from experiments using cetostearyl alcohol, i.e., a fixed HLB of 0.6, as the coemulsifier. Then, for a particular acyl lactylate, (e.g., sodium lauroyl lactylate having a fixed lactylate index of 76), the dependence between acyl lactylate concentration and a coemulsifier HLB value is:

$$C_L = 21.08 - (5.2 \times HLB_{co})$$

This equation shows that the concentration of the acyl lactylate in the emulsifier blend decreases as the HLB of the coemulsifier system increases. This is illustrated in the data in Table 8, which was generated by varying the coemulsifier HLB by blending cetostearyl alcohol with glyceryl monostearate.

TABLE 8

| HLB of Coemulsifier | Concentration of Sodium Lauroyl Lactylate in the Emulsifier Blend |
|---|---|
| 0.6 | 17.96 wt % |
| 1.8 | 11.72 wt % |
| 2.5 | 8.34 wt % |

More generally, the percentage by which the acyl lactylate concentration is lowered as the HLB of the coemulsifier increases (e.g., 70% of the original) correlates as:

$$\text{Percentage} = 117.23 - (28.5 \times HLB),$$

or as a fraction F $$F = 1.1723 - 0.285 \, HLB.$$

The data is summarized in Table 9. Combining these formulas with the original correlation derived using a coemulsifier having an HLB of 0.6 gives:

$$C_L = (105.34 - 1.15 LI)(1.1723 - 0.285 \, HLB)$$

or $$C_L = 123 - (30.54 \, HLB) - (1.35 \, LI) + (0.34 \, HLB \times LI).$$

It should be noted that to achieve the preselected viscosity for the o/w emulsion, it is not necessary to exactly satisfy the above equation, but only to substantially satisfy the equation, i.e., the weight percent of primary emulsifier in the emulsion blend can vary from about 0.9 $C_L$ to about 1.1 $C_L$, and preferably about 0.95 $C_L$ to about 1.05 $C_L$.

TABLE 9

| HLB of Coemulsifier | Concentration of Sodium Lauroyl Lactylate in the Emulsifier Blend as a Fraction of Concentration (HLB 0.6) |
|---|---|
| 0.6 | 100% |
| 1.8 | 66.29% |
| 2.5 | 47.17% |

The corresponding viscosity data for Tables 8 and 9 are shown in Table 10, and reveal that o/w emulsion viscosity decreases in a linear fashion as the HLB of the coemulsifier rises.

TABLE 10

| HLB of Coemulsifier | Viscosity (Pa.s) of a Balanced Base Formulation Using Sodium Lauroyl Lactylate |
|---|---|
| 0.6 | 12.23 |
| 1.8 | 8.87 |
| 2.5 | 7.01 |

The LI gives a formulator three ways to design a final o/w emulsion having a preselected rheology, prior to an optional fine tuning with hydrocolloids or other rheological additives: (a) the choice of acyl lactylate based on LI values, which defines, in large measure, where the o/w emulsion resides on the cream-to-lotion continuum, as long as coemulsifier HLB is fixed; (b) once a lactylate index is selected, viscosity of the o/w emulsion can be fine-tuned upwards by lowering the HLB of the coemulsifier, and (c) viscosity can be fine-tuned downwards by lowering the total concentration of the emulsifier blend (i.e., the acyl lactylate and coemulsifier, in a balanced ratio) according to the relationship:

$$\log \eta \propto c_E,$$

wherein η is o/w emulsion system viscosity, and $C_E$ is the total emulsifier blend concentration in the emulsion.

The choice of desired an acyl lactylate or acyl lactylate mixture using the LI simultaneously determines the optimum level of acyl lactylate used in the emulsifier blend. Thus, the lactylate index accounts for both the amount of gel network swelling achieved at an optimum use level of the acyl lactylate (the system viscosity), and the efficiency of swelling (optimum use level), and offers an easy-to-use method of formulating o/w emulsions of preselected viscosity with acyl lactylates, and replacing other primary emulsifiers in existing o/w emulsifiers with acyl lactylates.

Figure 6A:
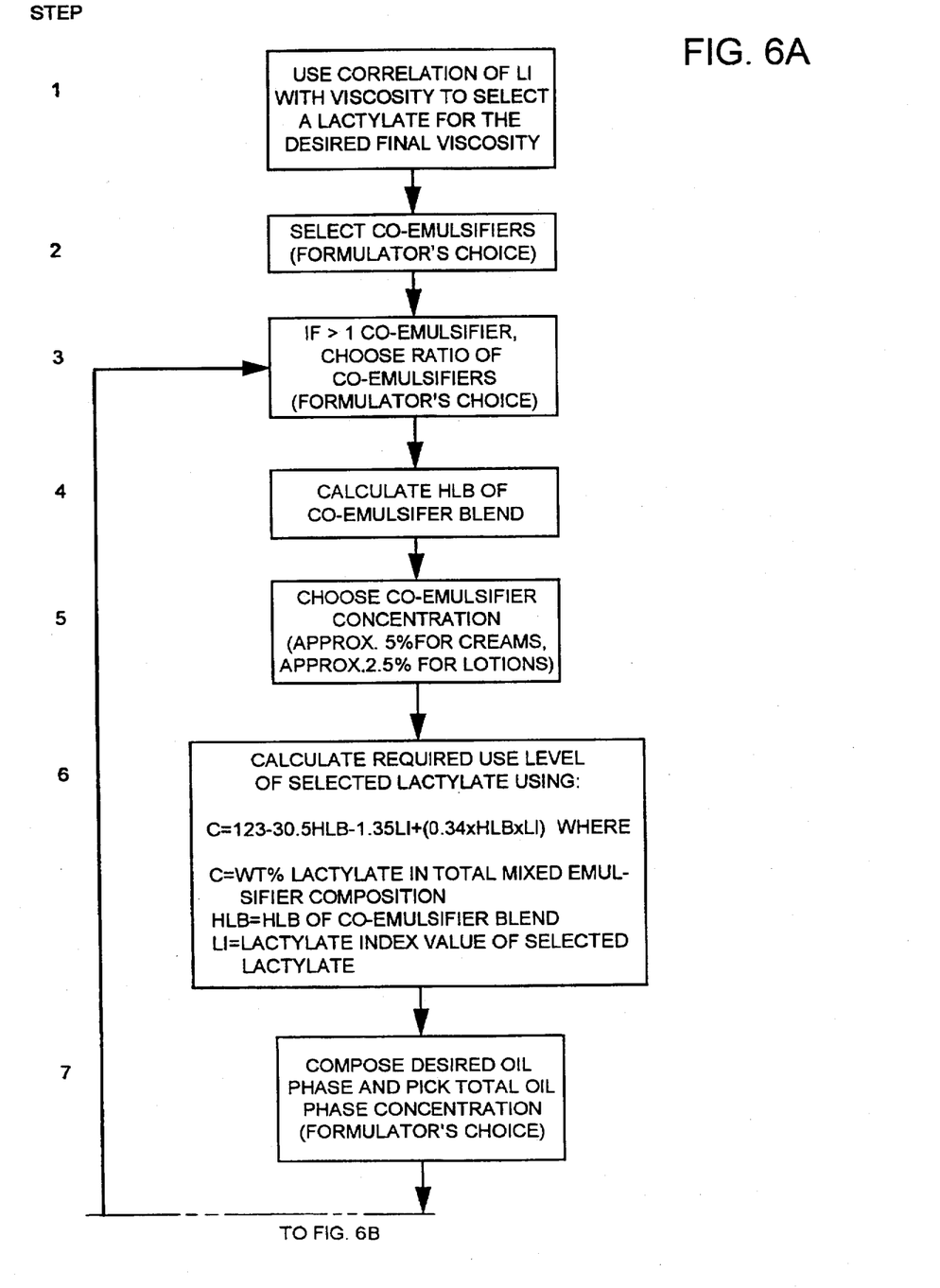
FIG. 6 is a flow chart outlining a method of formulating an o/w emulsion of preselected viscosity using the LI.
Figure 6B:
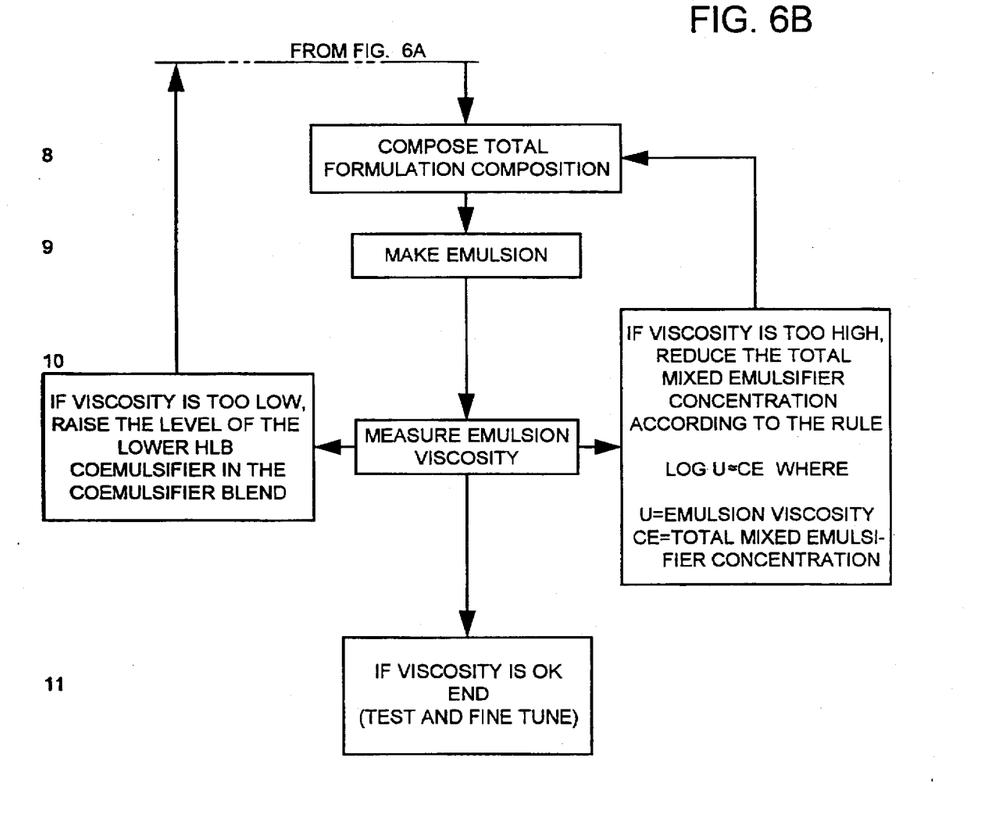

FIG. 6 is a flow sheet outlining a method of formulating an o/w emulsion using the lactylate index. The flow sheet is explained in the following example.

A formulator wishes to duplicate a cream-like composition having the following ingredients, in a descending weight percentage: water, glyceryl stearate, capric/caprylic triglyceride, cetearyl alcohol, glycerin, ceteareth-12, myristyl myristate, dimethicone, tocopheryl acetate, avocado oil, pecan oil, methyl paraben, carbomer, retinyl palmitate, propyl paraben, fragrance. The formulator also wishes to design a lotion that is similar to the cream-like composition. The formulator, therefore, first lists the composition ingredients according to function in the cream-like composition:

| Emulsifiers | Carrier/Optional Ingredient | Oil Phase/Option Ingredients |
|---|---|---|
| glyceryl stearate | water | capric/caprylic tri-glyderide |
| cetearyl alcohol | glycerin | myristyl myristate |
| ceteareth-12 | methyl paraben | dimethicone |
|  | carbomer | tocopheryl acetate |
|  |  | avocado oil |
|  |  | pecan oil |
|  |  | retinyl palmitate |
|  |  | propyl paraben |

Glyceryl stearate and cetearyl alcohol are low HLB compounds, and, in combination, are considered the coemulsifier. Cetearth-12 is a high HLB compound and is considered the primary emulsifier.

The formulator then performs the following steps: (a) because the emulsion is a cream, the formulator uses FIG. 4 or 5 and selects an acyl lactylate having an LI value between 55 and 65, e.g., sodium behenoyl lactylate (SBL) (LI value of 56) to replace the ceteareth-12 as the primary emulsifier; (b) the coemulsifier can remain a blend of glyceryl stearate and cetearyl alcohol because the choice of coemulsifier is not limited; (c) in this example, the formulator then arbitrarily chooses a 1:1 ratio of glyceryl stearate and cetearyl alcohol as the coemulsifier; (d) the formulator next calculates the HLB value of the coemulsifier, in this example, the HLB value of the coemulsifier is 1.9 because glyceryl stearate has an HLB value of 3.2 and cetearyl alcohol has an HLB value of 0.6; (e) because the o/w emulsion is a cream, the formulator selects 5% as the concentration of coemulsifier in the o/w emulsion (about 3.5% to about 7% by weight coemulsifier in an o/w emulsion provides a cream-like composition); (f) then the formulator calculates the amount of acyl lactylate, i.e., the amount of SBL, to use in the emulsifier blend from the formula:

$C_L = 123 - (30.54 \text{ HLB}) - (1.35 \text{ LI}) + (0.34 \text{ HLB} \times \text{LI})$, i.e., $C_{SBL} = 123 - (30.54 \times 1.9) - (1.35 \times 56) + (0.34 \times 1.9 \times 56) = 25.5\%$.

Therefore, the amount of SBL in the emulsifier blend is 25.5% by weight of the emulsifier blend, or to substantially satisfy the equation about 22.95% to about 28.05% by weight. Because 5 wt % of coemulsifier will be present in the final o/w emulsion, 1.67 wt % of the sodium behenoyl lactylate (25.5% by weight of the emulsifier blend) is used in conjunction with the coemulsifier; (g) the components of the oil phase admixed, wherein any oil phase concentration can be used, but to accommodate composition economics and efficacy, the formulator uses 15% total oil phase; (h) the final formulation is calculated:

| Phase A | |
|---|---|
| SBL | 1.67 |
| Glycerin stearate | 2.50 |
| Cetearyl alcohol | 2.50 |
| Oil phase | 15.00 |
| Phase B | |
| Glycerin | 3.00 |
| Methyl paraben | qs |
| Carbomer | 0.15 |
| Water to | 100.00 |
| Phase C | |
| Fragrance | qs; |

(i) an emulsion is prepared by first heating Phase A and Phase B to 75° C., then adding Phase A to Phase B, homogenizing, cooling to 30° C., and adding Phase C to the cooled mixture; and (j) measuring the viscosity of the o/w emulsion and fine tuning, as desired, as set forth in the flow chart.

A lotion-like composition is similarly prepared except: (a) an acyl lactylate having an LI value of about 65 to about 80 is selected (see FIGS. 4 and 5), and the formulator selects 2.5 wt % as the concentration of coemulsifier in the total o/w emulsion (1% to 3.5% coemulsifier provides a lotion composition). The concentration of acyl lactylate is calculated in the same way as for the cream-like composition using the LI value for the selected acyl lactylate.

The above tests show that acyl lactylates have been classified according to the structure of their hydrocarbon chain and the identity of the cationic counterion. This classification, termed the "lactylate index," allows a formulator to choose a particular acyl lactylate that satisfies the needs in the formulation. It has been found that acyl lactylates having carbon chain length of $C_{12}$ and below have disadvantages when used alone (i.e., decreased emulsion stability and viscosity) in an o/w emulsion. However, such acyl lactylates can be used in combination with longer hydrocarbon chain acyl lactylates, like behenoyl or stearoyl lactylate, to produce stable o/w emulsions of preselected viscosity.

Furthermore, it has been shown that acyl lactylates are highly efficient primary emulsifiers, when combined with gel network formers (i.e., coemulsifiers), especially at an optimum ratio. The same emulsifier blend can be used to prepare stable cream and lotion o/w emulsions by simply adjusting the amount of emulsifier blend present in the final o/w emulsion. In comparison to other ionic emulsifiers, such as phosphate esters, the acyl lactylates form o/w emulsions exhibiting small, evenly distributed droplets. Acyl lactylates also can be formulated with any type of oil phase, even with difficult to emulsify oil phases, such as silicones, and are considered as highly efficient emulsifiers.

It should be understood that the foregoing detailed description is given merely by way of illustration. Obviously, many modifications and variations of the invention as hereinbefore set forth can be made without departing from the spirit and scope thereof, and, therefore, only such limitations should be imposed as are indicated by the appended claims.

What is claimed is:

1. A balanced emulsifier blend for an oil-in-water emulsion having a preselected viscosity of about 2 to about 45 Pa.s, said emulsifier blend comprising:

(a) about 1% to about 70 by weight of the oil-in-water emulsion of a coemulsifier capable of forming a gel network in an aqueous phase and having an HLB value of about 0 to about 6; and (b) an acyl lactylate having a general structural formula:

wherein the RCO radical is a $C_6$ to $C_{22}$ acyl radical; a is a number from 1 to 3; and M is selected from the group consisting of an alkali metal, an alkaline earth metal, ammonium, and a substituted ammonium group having one or more $C_1$ to $C_3$ alkyl or hydroxyalkyl groups, and having a lactylate index value of about 50 to about 80 as a primary emulsifier, wherein the acyl lactylate is capable of providing the preselected viscosity and is selected to substantially satisfy a relation $$\log \eta = 12.6 - (0.16 \times LI),$$

wherein $\eta$ is the preselected viscosity in Pa.s and LI is the lactylate index value of the acyl lactylate;

and wherein the acyl lactylate is present in a sufficient amount to provide the preselected viscosity, said sufficient amount of acyl lactylate determined by substantially satisfying a formula:

$$C_L = 123 - (30.54 \text{ HLB}) - (1.35 \text{ LI}) + (0.34 \text{ HLB} \times LI),$$

wherein $C_L$ is the weight percent of the acyl lactylate in the emulsifier blend, HLB is the HLB value of the coemulsifier, and LI is the lactylate index value of the acyl lactylate.

2. The emulsifier blend of claim 1 wherein the preselected viscosity of the emulsion is about 10 to about 45 Pa.s, and the coemulsifier is present in an amount of about 3.5% to about 7% by weight of the emulsion.

3. The emulsifier blend of claim 2 wherein the acyl lactylate has a lactylate index value of about 56 to about 66.

4. The emulsifier blend of claim 1 wherein the preselected viscosity of the emulsion is about 2 to about 10 Pa.s, and the coemulsifier is present in an amount of about 1% to about 3.5% by weight of the emulsion.

5. The emulsifier blend of claim 4 wherein the acyl lactylate has a lactylate index value of about 66 to about 80.

6. The emulsifier blend of claim 1 wherein the coemulsifier is selected from the group consisting of a fatty acid, a fatty alcohol, a glyceryl fatty acid ester, a sorbitan fatty acid ester, a polyglyceryl fatty acid ester, a methyl glucoside fatty acid ester, nonionic surfactant having an HLB value of about 0 to about and mixtures thereof.

7. The emulsifier blend of claim 1 wherein the coemulsifier is a solid compound.

8. The emulsifier blend of claim 1 wherein the RCO radical is a $C_{12}$ to $C_{22}$ acyl radical.

9. The emulsifier blend of claim 1 wherein the acyl lactylate comprises an acyl lactylate analog wherein at least a portion of lactic acid in the acyl lactylate is substituted with an $\alpha$-hydroxy acid different from lactic acid, an amino acid, or a mixture thereof.

10. The emulsifier blend of claim 9 wherein the $\alpha$-hydroxy acid is selected from the group consisting of glycolic acid, citric acid, tartaric acid, malic acid, ethylglycolic acid, mandelic acid, leucic acid, and mixtures thereof.

11. The emulsifier blend of claim 9 wherein the amino acid is selected from the group consisting of alanine, glutamic acid, threonine, proline, leucine, glycine, tyrosine, lysine, and mixtures thereof.

12. The emulsifier blend of claim 1 wherein the acyl lactylate is a blend of two or more acyl lactylates.

13. A method of preparing an oil-in-water emulsion having a preselected viscosity comprising the steps of:

(a) selecting a coemulsifier, said coemulsifier capable of forming a gel network in an aqueous phase;

(b) selecting an acyl lactylate as a primary emulsifier, said acyl lactylate having a lactylate index value of about 50 to about 80, and capable of providing the preselected viscosity by substantially satisfying a relation $$\log \eta = 12.6 - (0.16 \times LI),$$

wherein $\eta$ is the preselected viscosity in Pa.s and LI is the lactylate index value of the acyl lactylate;

(c) calculating an amount of the acyl lactylate capable of providing the determined viscosity, said amount determined by substantially satisfying a formula:

$$C_L = 123 - (30.54 \text{ HLB}) - (1.35 \text{ LI}) + (0.34 \text{ HLB} \times LI),$$

wherein $C_L$ is the weight percent of the acyl lactylate in the emulsifier blend, HLB is the HLB value of the coemulsifier, and LI is the lactylate index value of the acyl lactylate;

(d) admixing the coemulsifier and the acyl lactylate to form a balanced emulsifier blend; and (e) admixing the balanced emulsifier blend, an oil phase, and an aqueous carrier to form the oil-in-water emulsion of preselected viscosity.

14. The method of claim 13 wherein the oil phase is selected from the group consisting of a volatile silicone compound, a nonvolatile silicone compound, a volatile hydrocarbon compound, a nonvolatile hydrocarbon compound, a triglyceride, a natural ester oil, an ester having about 10 to about 32 carbon atoms, a micropigment, and mixtures thereof.

15. The method of claim 13 wherein the oil phase comprises an essential oil, a naturally occurring oil, or a mixture thereof.

16. The method of claim 13 wherein the oil phase comprises an ultraviolet light absorber.

17. The method of claim 16 wherein the oil phase is present in an amount of about 0.5% to about 25% by weight of the oil-in-water emulsion.

18. The method of claim 13 wherein the acyl lactylate has the general structural formula:

wherein RCO radical is a $C_6$ to $C_{22}$ acyl radical; a is a number from 1 to 3; and M is selected from the group consisting of an alkali metal, an alkaline earth metal, ammonium, and a substituted ammonium group having one or more $C_1$ to $C_3$ alkyl or hydroxyalkyl groups.

19. The method of claim 13 wherein the acyl lactylate comprises an acyl lactylate analog wherein at least a portion of lactic acid in the acyl lactylate is substituted with an $\alpha$-hydroxy acid different from lactic acid, an amino acid, or a mixture thereof.

* * * * *

UNITED STATES PATENT AND TRADEMARK OFFICE
CERTIFICATE OF CORRECTION

PATENT NO. : 5,744,062
DATED : April 28, 1998
INVENTOR(S) : Gerd H. Dahms et al.

It is certified that error appears in the above-identified patent and that said Letters Patent is hereby corrected as shown below:

Column 5, line 35, "250°C" should be --25°C--

Column 8, line 2, "$C_{13}$-$C_4$" should be -- $C_{13}$-$C_{14}$ --

Column 8, line 13, "400 Cs" should be --400 cs--

Column 8, line 37, "diand" should be -- di- and --

Column 10, line 41, "COO-" should be -- COO⁻ --

Column 11, line 47, "(-10) =" should be -- (-10)) = --

Column 12, line 40, "viscosity, and n viscosity" should be --and o/w emulsion viscosity,--

Column 13, between lines 62 and 64, insert the following formula:

-- $\log \eta = C_E \cdot K$, --

Column 16, line 63, "b lend," should be --blend,--

Column 20, line 50, "70" should be --7%--

Column 21, lines 35 & 36, delete "nonionic surfactant having an HLB value of about 0 to about"

Signed and Sealed this

Twenty-fourth Day of August, 1999

Attest:

Q. TODD DICKINSON

*Attesting Officer*    *Acting Commissioner of Patents and Trademarks*